US010711263B2

(12) United States Patent
Tsai et al.

(10) Patent No.: US 10,711,263 B2
(45) Date of Patent: Jul. 14, 2020

(54) METHOD FOR EXTRACTING POLYHYDROXYALKANOATES (PHAS)

(71) Applicant: National Chi Nan University, Nantou County (TW)

(72) Inventors: Yung-Pin Tsai, Nantou County (TW); Meng-Shan Lu, Kaohsiung (TW); Chih-Chi Yang, Miaoli County (TW); Hao Shiu, New Taipei (TW); Jan-Wei Lin, Nantou County (TW)

(73) Assignee: NATIONAL CHI NAN UNIVERSITY, Nantou County (TW)

( * ) Notice: Subject to any disclaimer, the term of this patent is extended or adjusted under 35 U.S.C. 154(b) by 332 days.

(21) Appl. No.: 15/868,260

(22) Filed: Jan. 11, 2018

(65) Prior Publication Data
US 2019/0127727 A1   May 2, 2019

(30) Foreign Application Priority Data
Nov. 2, 2017   (TW) ............................. 106137883 A

(51) Int. Cl.
*C12N 13/00* (2006.01)
*C08G 63/89* (2006.01)
(Continued)

(52) U.S. Cl.
CPC ............... *C12N 13/00* (2013.01); *C02F 1/26* (2013.01); *C02F 11/006* (2013.01); *C08G 63/89* (2013.01); *C12N 1/06* (2013.01); *C02F 11/12* (2013.01); *C02F 2103/003* (2013.01); *C02F 2103/20* (2013.01); *C02F 2103/30* (2013.01);
(Continued)

(58) Field of Classification Search
CPC . C12N 13/00; C12N 1/06; C02F 11/12; C02F 2103/30; C02F 1/26; C02F 11/006; C02F 2103/003; C02F 2103/20; C02F 2209/44; C02F 2201/46135;
(Continued)

(56) References Cited

U.S. PATENT DOCUMENTS

| | | | |
|---|---|---|---|
| 7,378,266 B2 | 5/2008 | Narasimhan et al. | |
| 2012/0006754 A1* | 1/2012 | Tsai | ......................... C02F 9/00 |
| | | | 210/713 |

(Continued)

FOREIGN PATENT DOCUMENTS

TW    I399345    6/2013

*Primary Examiner* — Cameron J Allen
(74) *Attorney, Agent, or Firm* — Muncy, Geissler, Olds & Lowe, P.C.

(57) ABSTRACT

The present invention provides a method for extracting polyhydroxyalkanoates (PHAs), which comprises a pre-process step and an extraction step: removing water from waste sludge containing microorganisms in the pre-process step so that the waste sludge containing microorganisms has a water content of less than 40%; and applying a high-voltage pulsed electric field to the waste sludge during the extraction step to destroy the microorganisms and release the PHAs, wherein the high-voltage pulsed electric field is between 50 volts and 400 volts, an application time of the high-voltage pulsed electric field is between 5 seconds and 90 seconds, and an application frequency of the high-voltage pulsed electric field is between 500 Hz and 1000 Hz, thereby extracting the PHAs in the case of few chemicals.

6 Claims, 10 Drawing Sheets

(51) Int. Cl.
    *C12N 1/06*          (2006.01)
    *C02F 11/00*        (2006.01)
    *C02F 1/26*          (2006.01)
    *C02F 103/00*       (2006.01)
    *C02F 103/30*       (2006.01)
    *C02F 103/20*       (2006.01)
    *C02F 11/12*        (2019.01)

(52) U.S. Cl.
    CPC ............... *C02F 2201/46135* (2013.01); *C02F 2201/46175* (2013.01); *C02F 2209/02* (2013.01); *C02F 2209/06* (2013.01); *C02F 2209/44* (2013.01)

(58) Field of Classification Search
    CPC ........ C02F 2201/46175; C02F 2209/02; C02F 2209/06; C08G 63/89
    See application file for complete search history.

(56) References Cited

U.S. PATENT DOCUMENTS

2013/0199997 A1\*   8/2013   Werker ..................... C02F 3/12
                                                                      210/614
2018/0363013 A1\*   12/2018   Dijkman ................. C02F 3/006

\* cited by examiner

US 10,711,263 B2

METHOD FOR EXTRACTING POLYHYDROXYALKANOATES (PHAS)

FIELD OF THE INVENTION

The present application relates to an extraction process, and more particularly relates to a method for extracting polyhydroxyalkanoates (PHAs) from waste sludge.

BACKGROUND OF THE INVENTION

Polyhydroxyalkanoates (PHAs) are biosynthetic plastic materials, and PHAs are capable of being synthesized through ingesting matrix by microbial species present in an environment containing a carbon source and limited nutrients, such as nitrogen, phosphorous, sulfur, oxygen, magnesium, etc. Its excellent thermoplasticity and biodegradability make it possible for the idea which replaces the petroleum-derived plastic with this biosynthetic plastic.

As a result, many research groups have devoted their research to this and have proposed various methods for extracting PHAs. For example, U.S. Pat. No. 7,378,266 provides an improved Process for the solvent-based extraction of PHAs from biomass, comprising the steps of: a) combining the biomass containing the PHAs with a solvent selected from lower chain ketones, and mixtures thereof to form a biomass liquor wherein the biomass liquor comprises less than about 25% water; b) mixing the biomass liquor at a temperature in the range of from about 70° C. to about 120° C.; c) separating the PHAs from the biomass liquor to form a PHA-enriched liquor, wherein the separating occurs at a temperature of at least about 40° C.; d) mixing the PHA-enriched liquor with water to form precipitated PHAs and an impure solvent liquor, wherein the water is mixed with the PHA-enriched liquor in the ratio of from at least about 3 parts water to one part PHAs; and e) recovering the precipitated PHAs from the impure solvent liquor.

In addition, the Taiwan patent No. 1399345 provides a method for extracting polyhydroxyalkanoates from waste sludge, which is to measure the weight of the solid part in the sludge after removing of the sand grain from the collected waste sludge containing microbial cells, and carry out the steps of washing, water removal and freezing so as to stop the microbial cells activity; Subsequently, the sludge is made to carry out a pre-process step to destroy the cell bodies of the microbial cells in the waste sludge performed by freezing; and then the sodium hypochlorite aqueous solution is added into the sludge to prepare a sludge mixture with solid/liquid ratio at 0.67 to 4 mg/ml, so that the cell walls of the microbial cells are destroyed to release the polyhydroxyalkanoates. Finally, the sludge mixture is made to carry out a purification step to remove the non-polyhydroxyalkanoate substance and obtain a purified polyhydroxyalkanoates precipitate.

U.S. Pat. No. 7,378,266 discloses that extracts PHAs by solvent extraction from biological systems such as plants or bacteria. While the Taiwan Patent No. 1399345 can extract polyhydroxyalkanoate with high purity directly from the waste sludge without the condition of carrying out the pure culture. However, both the above two cases require the use of considerable amounts of chemicals to destroy microbial cells to achieve the purpose for extracting PHAs. Next, the current production costs of PHAs are very high, which limits the possibility of industrial production of PHAs and cannot be widely used. In addition, general chemical extraction process need more time, and are not advantageous to commercialization. As a result, there is an urgent need to develop a more economical method of producing PHAs, both the steps and costs thereof meet the requirements of the acceptable range of industrial production.

SUMMARY OF THE INVENTION

The main purpose of the present invention is to simultaneously solve the drawbacks of the conventional method for extracting PHAs, which are the high costs consumed and the environmental damage caused by extensive use of chemicals.

In order to achieve the above purpose, the present invention provides a method for extracting PHAs, comprising: a pre-process step of removing water from the waste sludge containing microorganisms so that the waste sludge has a water content of less than 40%; and an extraction step: performing with a electroporation, applying a high-voltage pulsed electric field to the waste sludge to destroy the microorganisms and release PHAs, wherein the high-voltage pulsed electric field is between 50 volts and 400 volts, an application time of the high-voltage pulsed electric field is between 5 and 90 seconds, and an application frequency of the high-voltage pulsed electric field is between 500 and 1000 Hz.

In one embodiment of the present invention, the extraction step further includes a chemical extraction process, wherein the waste sludge is subjected to a primary extraction by the electroporation, and then subjected to a second extraction by the chemical extraction process.

In one embodiment of the present invention, an activation step is further included after the pre-process step. The activation step is to carry out a fermentation processing on the discarded sludge firstly, mix up water and the fermented waste sludge at a ratio of 1:1 and aerate such that the waste sludge has saturated dissolved oxygen content of more than 80%, an aerobic dynamic feeding (ADF) processing was performed.

Therefore, compared with the prior art, the beneficial effects of the present invention are that: the method for extracting PHAs of the present invention utilizes the electroporation for replacing the conventional technology which relies on chemicals to destroy microbial cells, and reduces the use of chemicals, it is an environmentally friendly PHAs extraction process.

DETAILED DESCRIPTION OF THE PREFERRED EMBODIMENTS

The detailed description and the technical content of the present invention will now be described in conjunction with the drawings as follows:

The First Embodiment

Figure 1:
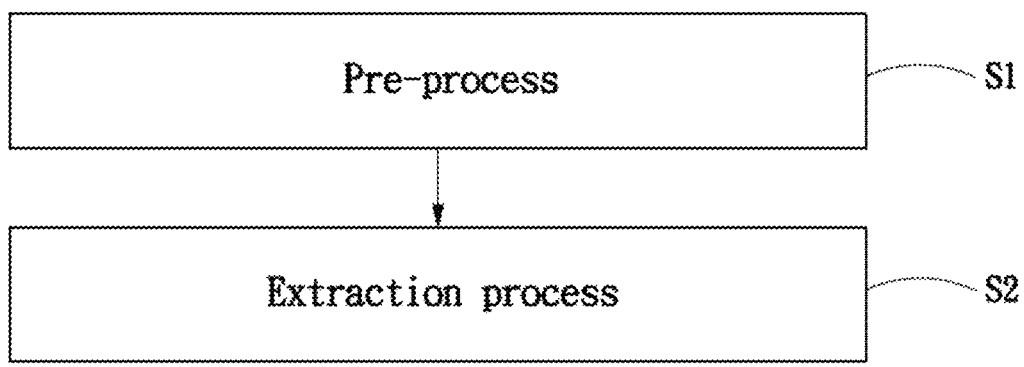
FIG. 1 is a flowchart of the method for extracting PHAs according to the first embodiment of the present invention.

FIG. 1 is a flowchart of the method for extracting PHAs according to an embodiment of the present invention. The method mainly includes a pre-process step (S1) and an extraction step (S2).

In the pre-process step (S1), the water is removed firstly from the waste sludge containing microorganisms so that the waste sludge has a water content of less than 40%. The above-mentioned "waste sludge containing microorganisms" may be waste sludge sampled from aerobic digestion troughs or sludge thickening troughs of domestic sewage, livestock husbandry, fermentation industry, medical institutions, optoelectronics, dyeing and finishing, or textile industry. The species of microorganism contained therein is not particularly limited, as long as the microorganism can accumulate, synthesize or decompose PHAs. As of now, more than 250 species of microorganisms including Gram-negative bacteria or Gram-positive bacteria have the ability, without limitation, examples include *Alcaligenes eutrophus*, *Alcaligenes latus* or *Azotobacter vinelandii* and the like. As for the methods of removing water, there is no particular limitation. For example, first let the waste sludge containing microorganisms stand for a period of time, after the solid precipitates, remove the supernatant liquid so that the water content of the waste sludge is less than 40%, such as 30%, 20%, or 10%, which is beneficial for subsequent extraction steps.

Subsequently, the extraction step (S2) is performed. In this embodiment, the extraction step (S2) is mainly a electroporation. The technical principle of the electroporation is to make microbial cells transiently produce some tiny pores by utilizing short-time large pulsed electric field, thereby achieving the effect of PHAs extraction.

The electroporation may operate to destroy the microbial cells by subjecting the waste sludge to a high-voltage electric field, the operational parameters thereof are at a frequency of 50 volts to 400 volts and at a frequency of 500 to 1000 Hz for 5 to 90 seconds to complete PHAs extraction. The electric field intensity of the high-voltage electric field may be more than 102 V/mm, but the present invention is not particularly limited, and can be adjusted according to the actual situation.

Figure 2A:
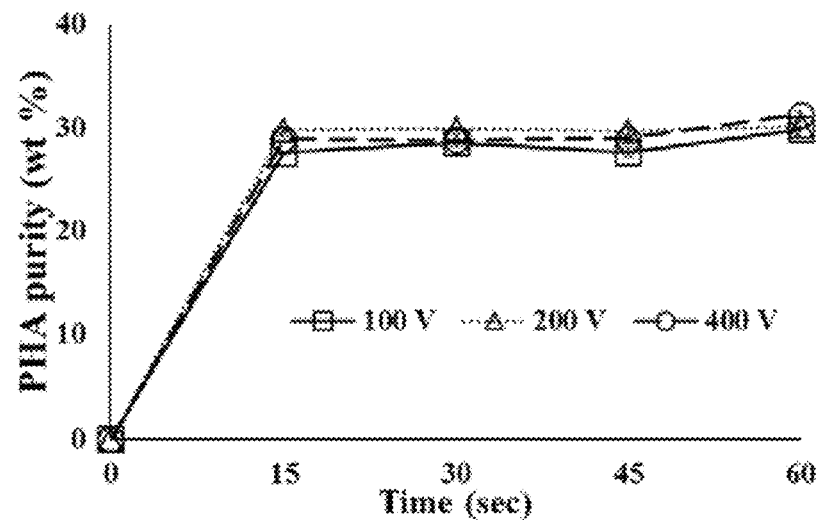
FIG. 2A is the results of the PHA purity of the method for extracting PHAs according to the first embodiment of the present invention.
Figure 2B:
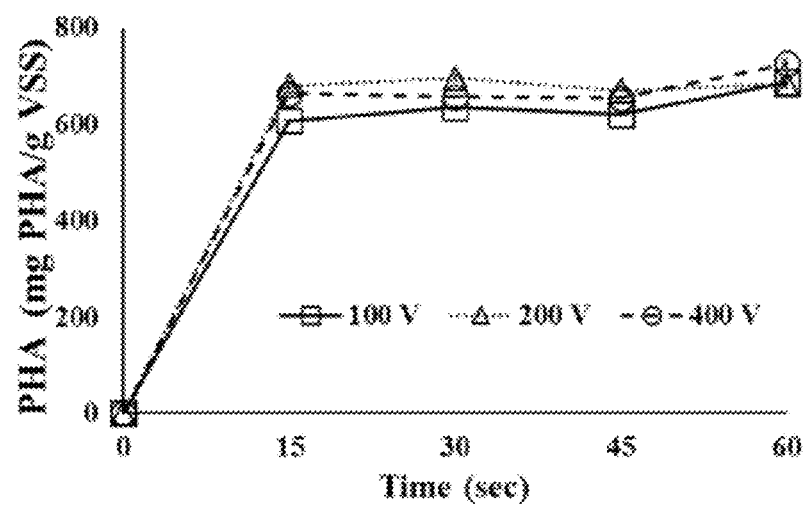
FIG. 2B is the results of PHAs content of the method for extracting PHAs according to the first embodiment of the present invention.
Figure 2C:
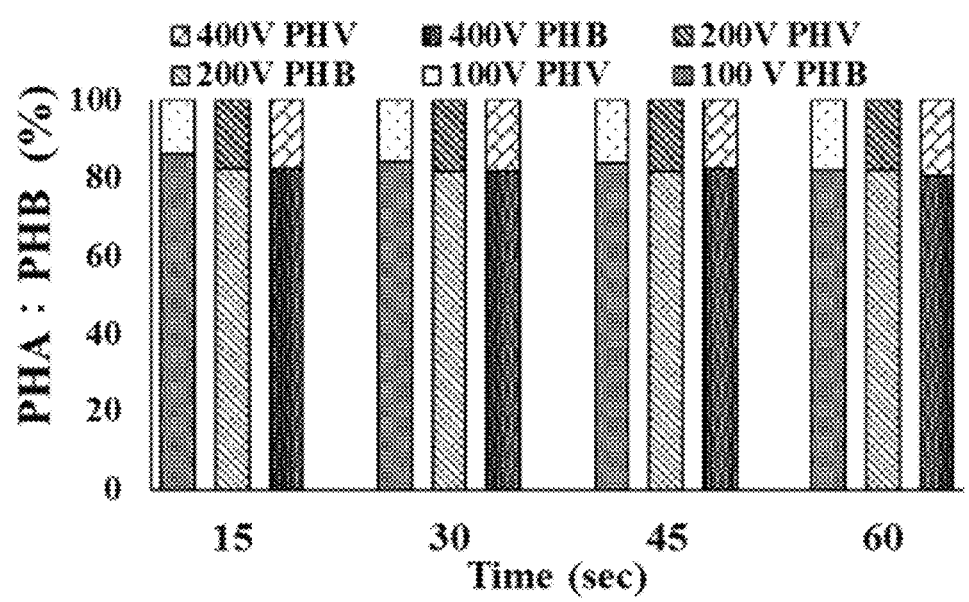
FIG. 2C is the results of the PHAs composition of the method for extracting PHAs according to the first embodiment of the present invention.

In one specific embodiment, when the operating parameters of the electroporation are 100V, 200V and 400V respectively, the time is set to 15 seconds, 30 seconds, 45 seconds and 60 seconds, and the frequency is set to 1000 Hz, measure the purity, content and their composition of PHAs, please refer to FIG. 2A, FIG. 2B, and FIG. 2C.

From the above results, it can be found that there is no significant influence on the purity and content of PHAs under the operating conditions of different parameters, the purity of PHAs is between 27.6±0.09 wt % and 31.3±0.33 wt %, and the content of PHAs is between 608±0.16 to 727±6.89 mgPHA/gVSS. The composition of PHAs is further analyzed, the results found no significant effect.

The Second Embodiment

Figure 3:
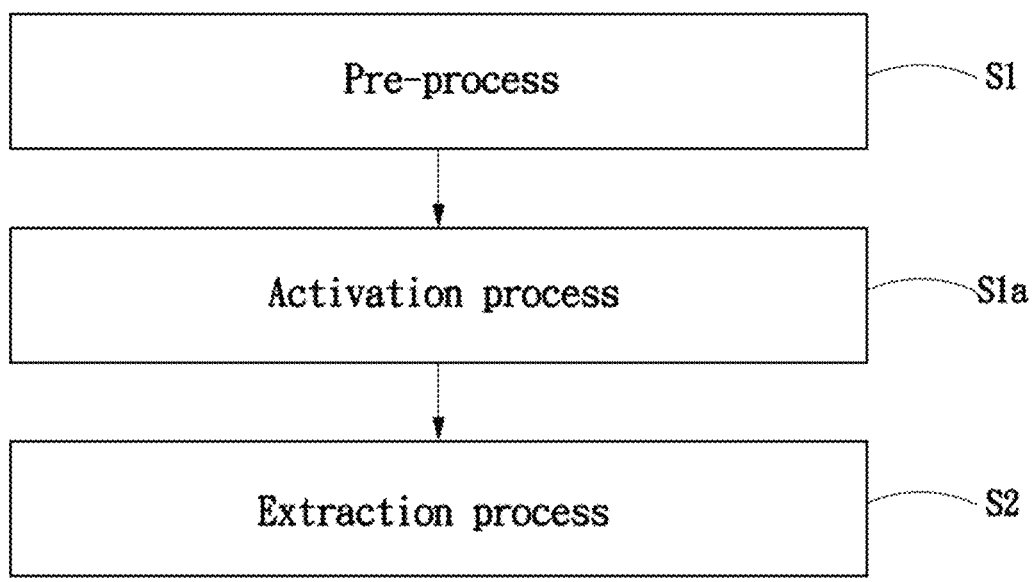
FIG. 3 is a flowchart of the method for extracting PHAs according to the second embodiment of the present invention.

Regarding the second embodiment of the present invention, the method for extracting PHAs is shown in the flowchart of FIG. 3, the differences from that of the first embodiment lies in, in addition to a chemical extraction process in the extraction step (S2), an activation step (S1a) is further included between the pre-process step (S1) and the extraction step (S2) to increase the content of PHAs.

The pre-process step (S1) of the second embodiment is the same as that of the first embodiment, both of them make the water content of the waste sludge is less than 40% so as to be advantageous to carry out the subsequent extraction steps, which will not be repeated here.

This activation step (S1a) which is subsequently carried out aims to increase the amount of the PHAs accumulated by microorganisms in the waste sludge. First, the waste sludge is subjected to a fermentation processing which carries out fermentation through adjusting the pH value of the waste sludge at about pH=11±0.5, and then incubating at a temperature of 20° C. to 50° C. for about 2 to 7 days. In a preferred embodiment, the fermentation processing is placed in a constant temperature shaking incubator at 40° C. for about 5 days. Next, the fermented waste sludge is mixed with water at a ratio of 1:1 and aerated at 25° C. so that the waste sludge has a saturated dissolved oxygen content of 80% or more, and then an aerobic dynamic feeding (ADF) process is carried out.

The ADF is a practical application of feast and famine cycling, which is also a method that can increase the production and storage rate of PHAs in microorganisms. In this embodiment, the fermentation liquid generated after the fermentation processing is used as a processing liquid used in the ADF process. When using the fermentation liquid as a carbon source, it is not necessary to adjust the proportion of nitrogen and phosphorus in any liquid, and thus it can increase the PHAs yield by controlling the content of ammonia nitrogen and phosphorus in the fermentation liquid. The fermentation liquid includes at least two $C_2$-$C_6$ volatile fatty acids, and the $C_2$-$C_6$ volatile fatty acid may be selected from the group consisting of acetic acid, propionic acid, butyric acid and valeric acid. In this embodiment, the concentration of volatile fatty acids contained in the fermentation liquid is 400 mg/L, wherein the content of acetic acid and propionic acid is the highest. However, in the present invention, there are no special restrictions on the concentrations of all the volatile fatty acids and the proportions of these components in the fermentation liquid or the processing liquid.

In addition, in other embodiments, other processing liquids may also be used instead of having to use the aforementioned fermentation liquid. As long as the processing liquid includes at least two kinds of $C_2$-$C_6$ volatile fatty acids, the $C_2$-$C_6$ volatile fatty acids may be selected from the group consisting of acetic acid, propionic acid, butyric acid, and valeric acid.

At the same time as the processing liquid is added for the first time, the carbon source in the processing liquid enters the trough body, and then the amount of saturated dissolved oxygen decreases due to consumption of oxygen by the microorganism utilizing the carbon source in the processing liquid. When the carbon source is about to be used up, the saturated dissolved oxygen amount accordingly increases to 70%, the processing liquid is added for the second time, and the process is repeated several times. In a preferred embodiment, the processing liquid is added 5 times. However, the present invention is not limited thereto, and the number of times for adding the processing liquid may increase or decrease according to actual needs.

Then, the extraction step (S2) is performed after the aerobic dynamic feeding step. In the present embodiment, the extraction step (S2) comprises a electroporation and a chemical extraction process: firstly, the waste sludge is subjected to a high-voltage electric field using a electroporation at a frequency of 50V to 400V and a frequency of 500 to 1000 Hz for 5 to 90 seconds to destroy the microbial cells to complete a preliminary extraction step; Next, a second extraction is carried out by the chemical extraction process to destroy the microorganisms and release PHAs.

In this embodiment, the waste sludge can be centrifuged to remove the supernatant and placed in a freezer at −20° C., followed by further destroying microbial cells processed for 1 minute by ultrasonic pulverizer of which the power is 9 W, and then the surfactant (such as sodium lauryl sulfate) having a concentration of 1% (w/v) is added for performing the first process, the processing time may be between 15 and 60 minutes.

Subsequently, after the waste sludge was centrifuged at 3000 rpm for 20 minutes, the supernatant liquid was removed, and the sodium hypochlorite was added at a concentration of 5% (v/v) to 70% (v/v), and mixed evenly, the mixture was allowed to react for the second processing time. After another centrifugation at 3000 rpm for 20 minutes, the white powder at the bottom is PHAs. In this step, the ratio of the volume of the sodium hypochlorite solution added measured to the weight of the solid portion in the waste sludge is defined as "solid/liquid ratio of the waste sludge", it is preferably 1.00 mg/ml.

Since sodium hypochlorite has stronger oxidation ability, the main function in the extraction is to remove non-PHAs substances in the waste sludge. If the second reaction time is extended, the long chain PHAs will broke, and has an influence on the composition proportion of Polyhydroxybutyrate (PHB) and Polyhydroxyvalerate (PHV). In this embodiment, the second reaction time is 5 minutes to 3 hours depending on the circumstances and needs, and the present invention is not particularly limited in this regard.

Figure 4A:
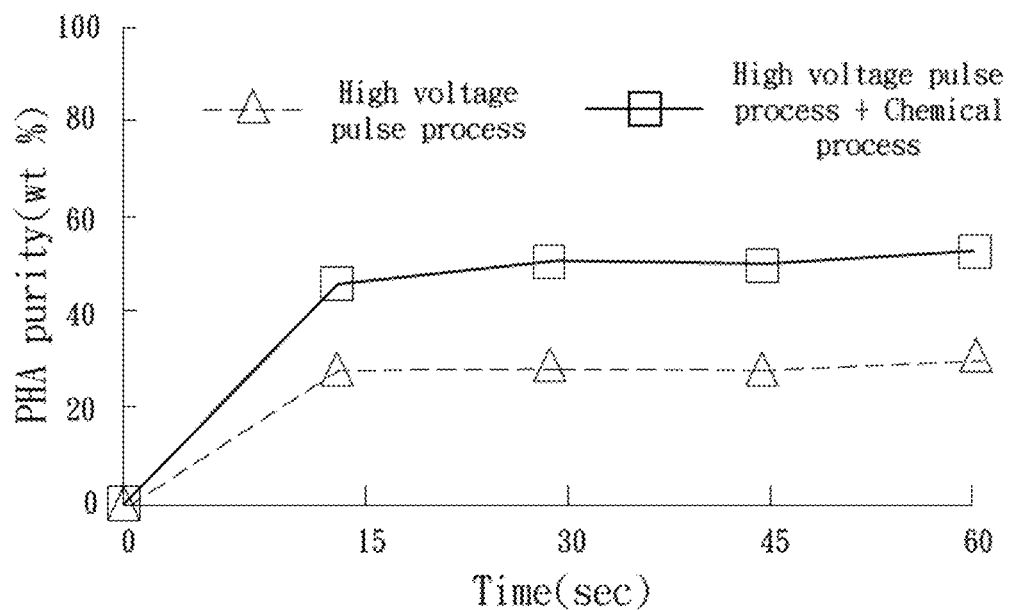
FIG. 4A is the results of the PHA purity of the method for extracting PHAs according to the second embodiment of the present invention.
Figure 4B:
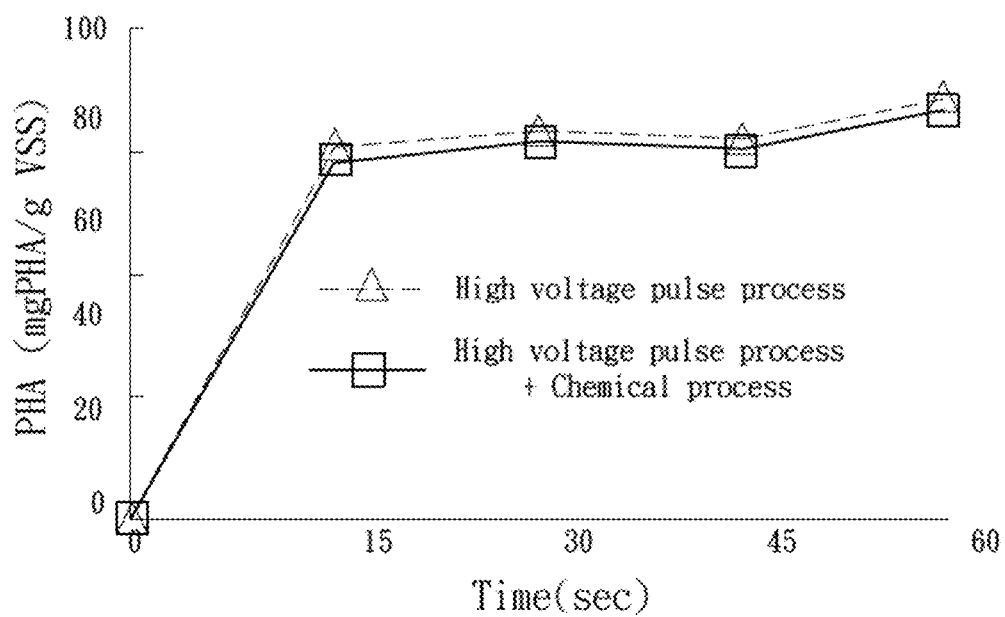
FIG. 4B is the results of the PHAs content of the method for extracting PHAs according to the second embodiment of the present invention.

In the second embodiment, a high-voltage electric field is applied to the waste sludge for 15 seconds by the electroporation under the operating conditions at a frequency of 100 volts and at a frequency of 1000 Hz. The chemical extraction process processes for 5 minutes under the operating conditions which utilizes the sodium hypochlorite solution having a concentration of 10% (v/v) in the case that the solid/liquid ratio of the waste sludge is 1.00 mg/ml. The results are shown in FIG. 4A and FIG. 4B. By combining this electroporation with the chemical extraction process, the results showed that the purity and content of PHAs obtained by the combined extraction process, which are 50.1±2.79 wt % and 620±35.58 mgPHA/gVSS respectively, are higher than the result of the PHAs obtained only by the electroporation (of which the PHAs purity is 28.5±1.04 wt % and the PHAs content is 638±35.21 mgPHA/gVSS).

The Third Embodiment

In the present embodiment, the operation of the electroporation is fine-tuned, and the influence of the operation parameters on the composition ratio of PHB and PHV in PHAs is considered.

Figure 5A:
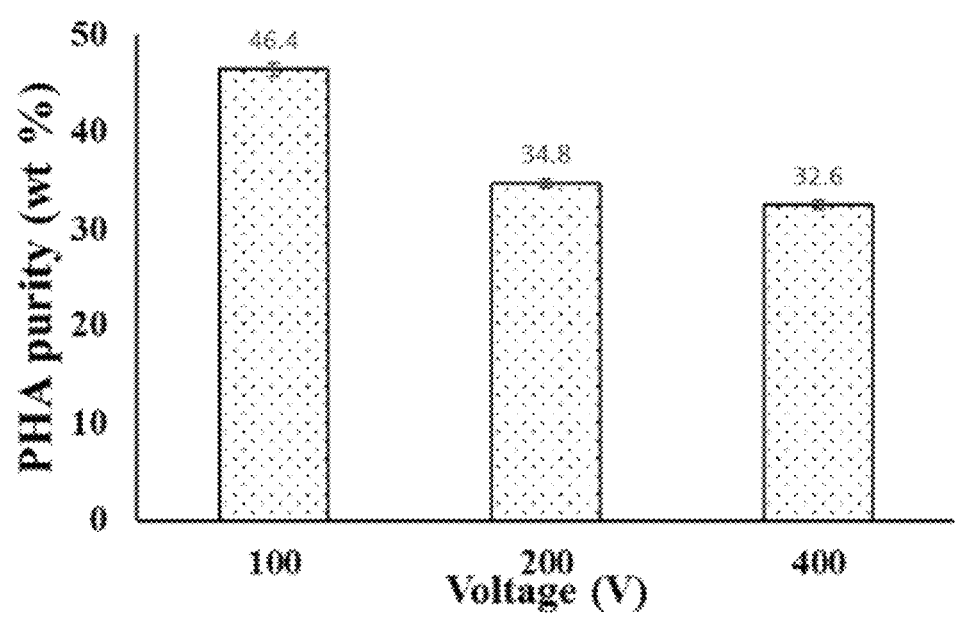
FIG. 5A is the results of the PHAs purity when the PHAs are extracted at different volts in the third embodiment of the present invention.
Figure 5B:
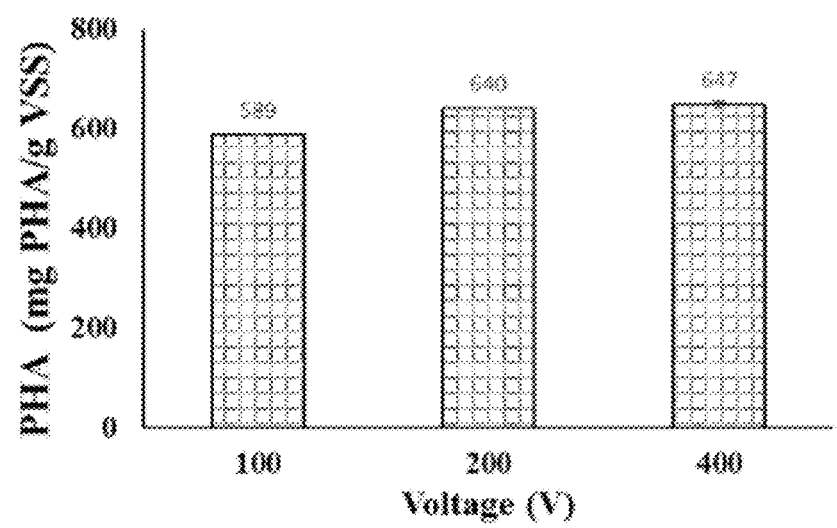
FIG. 5B is the results of PHAs content when the PHAs are extracted at different volts in the third embodiment of the present invention.
Figure 5C:
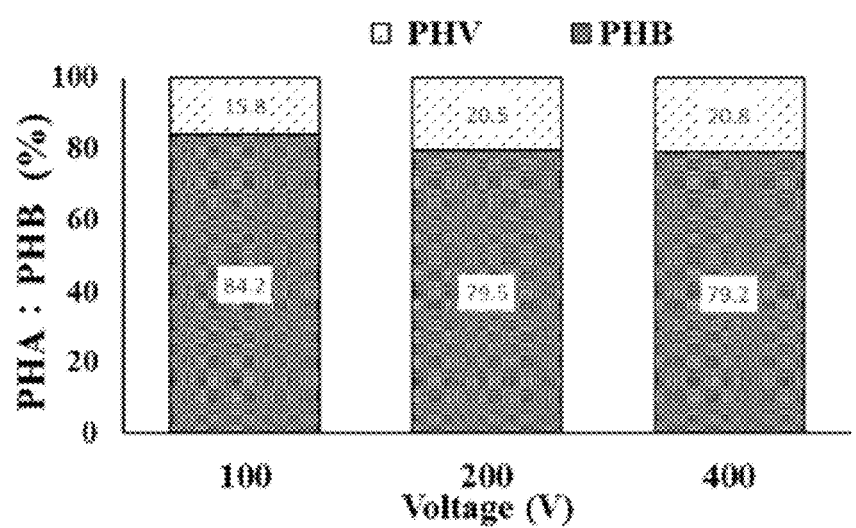
FIG. 5C is the results of the PHAs composition analysis when the PHAs are extracted at different volts in the third embodiment of the present invention.

First, the high-voltage pulsed electric field was applied to the waste sludge at 100V, 200V and 400V, respectively, when the high-voltage pulsed electric field was applied for 15 seconds at a frequency of 1000 Hz, and the purity, the content, and the composition of components of PHAs was measured at different values of voltage. Please refer to FIG. 5A, which shows that different volts have a significant effect on the purity of the extracted PHAs (P=0.001), and the purity of PHAs obtained at 100V is obviously higher than that of 200V and 400V. For the PHAs content, please refer to FIG. 5B. The obtained PHAs are 589±0.10 wt %, 640±0.49 wt % and 647±5.98 wt % respectively. The statistical verification results showed that the different volts have a significant effect on the content of the extracted PHAs (P=0.002). Though there was no significant difference between 200V and 400V, the content of the obtained PHAs at 200V and 400V was obviously higher than that of 100V. The PHAs composition is further discussed; different volts have no significant effect on the PHB and PHV composition, as shown in FIG. 5C.

Figure 6A:
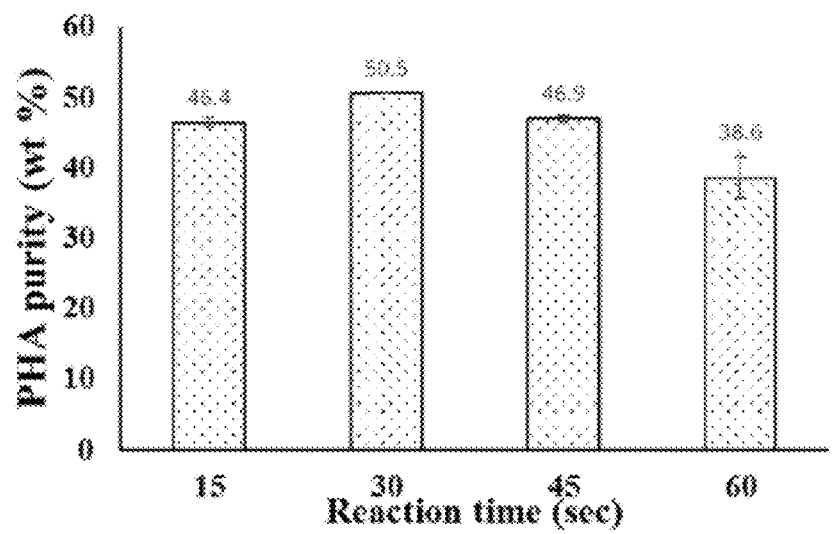
FIG. 6A is the results of the PHAs purity when the PHAs are extracted at different periods of time in the third embodiment of the present invention.

Next, the waste sludge is processed for 15 seconds, 30 seconds, 45 seconds and 60 seconds respectively at a frequency of 100V and 1000 Hz to carry out the PHAs extraction. For the purity of PHAs, please refer to FIG. 6A. The purities of the PHAs obtained at 15 seconds, 30 seconds and 45 seconds are significantly higher than that of 60 seconds, and no significant difference can be found among 15 seconds, 30 seconds and 45 seconds.

Figure 6B:
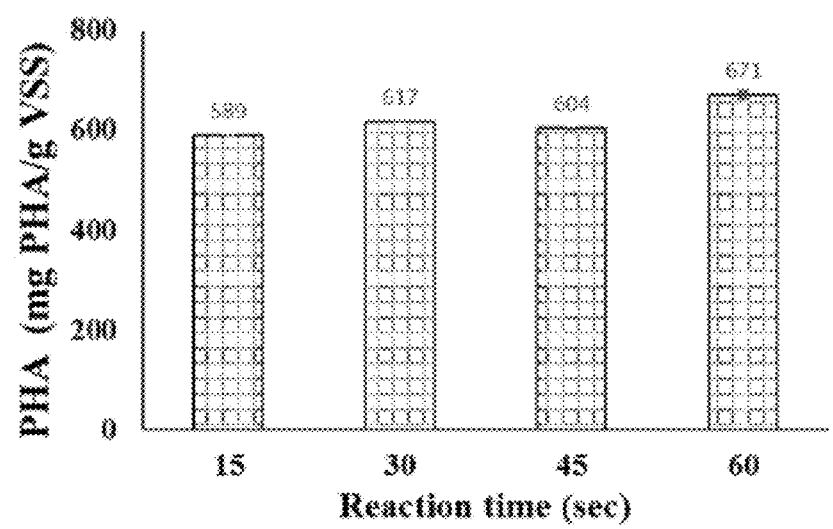
FIG. 6B is the result of the PHAs content when the PHAs are extracted at different periods of time in the third embodiment of the present invention.
Figure 6C:
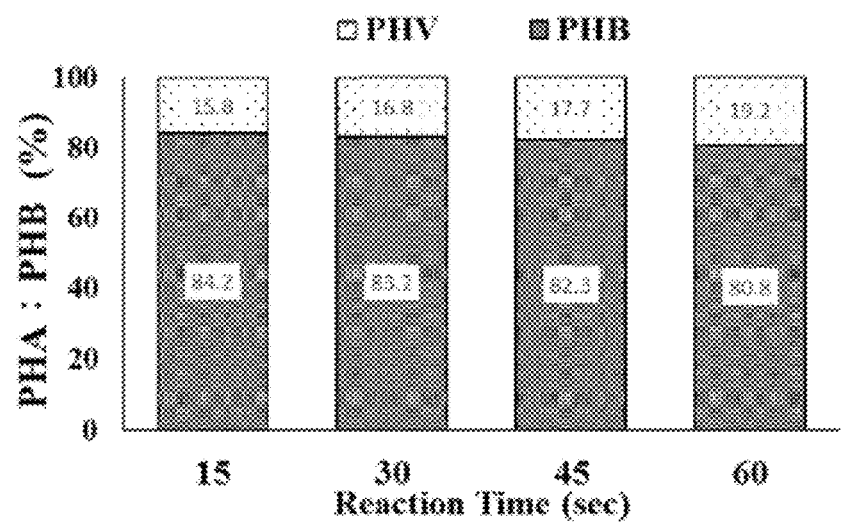
FIG. 6C is the results of the PHAs composition analysis when the PHAs are extracted at different periods of time in the third embodiment of the present invention.

FIG. 6B shows that when extracted at different periods of time, the content of PHAs is in the order of 60 seconds>30 seconds>45 seconds>15 seconds. The PHAs composition is further discussed, as shown in FIG. 6C, there is no significant effect on the PHB and PHV composition caused by the difference between the time.

Finally, the effects at different frequencies are discussed. The operating conditions used here are 100V for 30 seconds, and the frequency is 500 Hz, 666 Hz and 1000 Hz respectively.

Figure 7A:
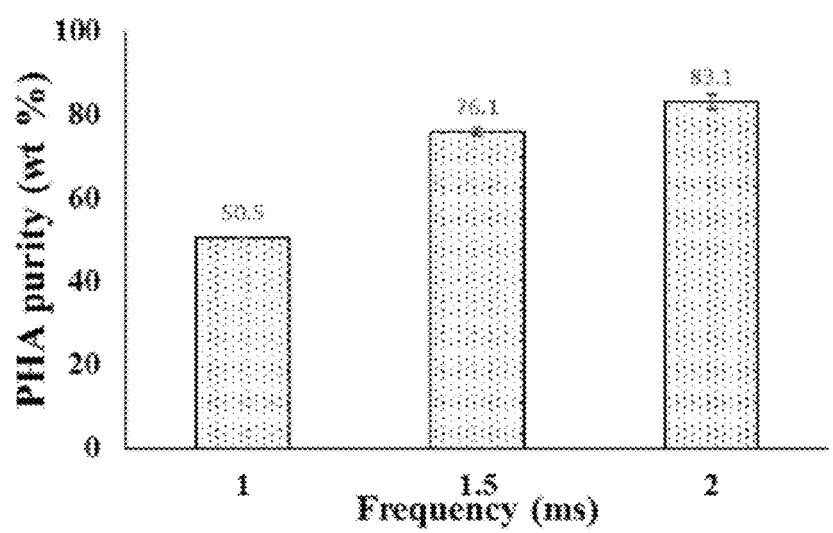
FIG. 7A is the results of PHAs purity when the PHAs are extracted at different frequencies in the third embodiment of the present invention.

Please refer to FIG. 7A, when the frequency are 500 Hz, 666 Hz and 1000 Hz respectively, the obtained PHAs have the purity of 50.5±0.01, 76.1±0.92 and 83.1±1.75 wt % respectively, and the statistical verification results show that different frequencies have a significant effect on the purity of the extracted PHAs (P=0.001), and the purity of PHAs increased with increasing frequency.

Figure 7B:
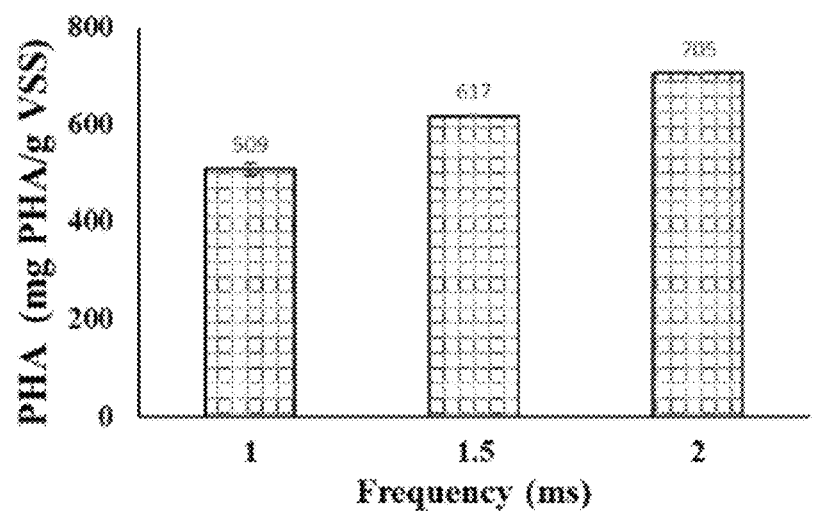
FIG. 7B is the results of the PHAs content when the PHAs are extracted at different frequencies in the third embodiment of the present invention.

In FIG. 7B, the purity of the PHAs is 509±14.10, 617±0.35 and 705±1.22 wt % respectively. The statistical verification results show that different frequencies also have significant effects on the content of the extracted PHAs (P=0.001), 500 Hz>666 Hz>1000 Hz.

Figure 7C:
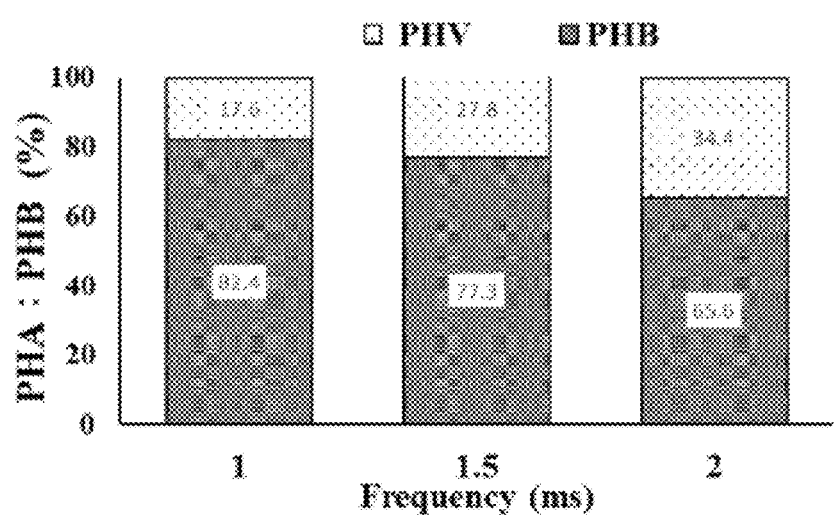
FIG. 7C is the results of the PHAs composition analysis when the PHAs are extracted at different frequencies in the third embodiment of the present invention.

The PHAs composition is further discussed, as shown in FIG. 7C, different frequencies also had a significant impact on the composition of PHB and PHV: with increasing frequency, the PHB ratio in PHA gradually decreased, while the PHV ratio increased. From the experimental results at different frequencies, it can be found that the optimum frequency is 500 Hz.

Based on the above test results, when the electroporation is adjusted, and a high-voltage electric field is applied to the waste sludge for 30 seconds at a frequency of 100V and 500 Hz, the purity of PHAs repeatedly measured through 15 times measurements falls in the range of 71.3% to 85.9%, which is not far from the purity of the PHAs obtained by simple chemical method.

Compared with the conventional method simply used chemical extraction process, the optimum operating conditions are that the sodium hypochlorite having a concentration of 60% (v/v), the sludge solid/liquid ratio of 1.00 mg/ml and the sodium hypochlorite immersion time of 60 minutes, respectively. In the present invention, the purity and the content of PHAs can be obtained by simply using the electroporation for the extraction of PHAs. If the electroporation and the chemical extraction process are further combined, the sodium hypochlorite concentration and the processing time are reduced to 10% (v/v) and 5 minutes. It is obvious that the present invention can effectively reduce the amount of chemicals used, has the potential of replacing the conventional technology to destroy the microbial cells in the prior art, and is an environmentally friendly PHAs extraction process.

What is claimed is:

1. A method for extracting polyhydroxyalkanoates (PHAs), comprising the following steps:
   a pre-process step: removing water from waste sludge containing microorganisms so that the waste sludge containing microorganisms has a water content of less than 40%; and
   an extraction step: by utilizing a electroporation, applying a high-voltage pulsed electric field to the waste sludge to destroy the microorganisms and release polyhydroxyalkanoates (PHAs), wherein the high-voltage pulsed electric field is between 50 volts and 400 volts, an application time of the high-voltage pulsed electric field is between 5 seconds and 90 seconds, and an application frequency of the high-voltage pulsed electric field is between 500 Hz and 1000 Hz.

2. The method of claim 1, the high-voltage pulsed electric field is applied to the waste sludge for 15 seconds to 60 seconds at a frequency of 100 volts to 400 volts and at a frequency of 500 to 1000 Hz.

3. The method of claim 1, the extraction step further comprising a chemical extraction process, wherein the waste sludge is subjected to a primary extraction by the electroporation, and then subjected to a second extraction by the chemical extraction process.

4. The method of claim 3, wherein the chemical extraction process is a surfactant-sodium hypochlorite extraction process, the waste sludge is processed firstly with a surfactant for a first processing time, and then the sodium hypochlorite is added to process the waste sludge for a second processing time, wherein the first processing time is from 15 minutes to 3 hours, and the second processing time is from 5 minutes to 3 hours.

5. The method of claim 4, wherein the surfactant is sodium lauryl sulfate, and a concentration of the surfactant is 1% (w/v).

6. The method of claim 4, wherein the sodium hypochlorite has a concentration of 5% (v/v) to 70% (v/v).

* * * * *